US006534220B2

(12) United States Patent
Garbe

(10) Patent No.: US 6,534,220 B2
(45) Date of Patent: Mar. 18, 2003

(54) HIGH-BOILING ELECTROLYTE SOLVENT

(75) Inventor: James E. Garbe, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 33 days.

(21) Appl. No.: 09/751,170

(22) Filed: Dec. 29, 2000

(65) Prior Publication Data

US 2002/0084445 A1 Jul. 4, 2002

(51) Int. Cl.[7] .................................................. H01M 6/16
(52) U.S. Cl. ...................... 429/342; 252/62.2; 252/364; 429/46; 429/340; 558/276; 560/33
(58) Field of Search ........................ 558/276; 560/165, 560/33; 429/46, 340, 342; 252/364, 62.2

(56) References Cited

U.S. PATENT DOCUMENTS

| | | | | |
|---|---|---|---|---|
| 3,014,807 A | * | 12/1961 | Beinfest et al. | ......... 252/364 X |
| 3,185,590 A | | 5/1965 | Mayer et al. | |
| 3,663,604 A | * | 5/1972 | Blöchl | |
| 3,778,310 A | | 12/1973 | Garth | |
| 3,877,983 A | | 4/1975 | Hovsepian | |
| 4,163,829 A | | 8/1979 | Kronenberg | ................. 429/194 |
| 4,511,730 A | * | 4/1985 | Fields | .................... 560/165 X |
| 4,690,877 A | | 9/1987 | Gabano et al. | ............. 429/194 |
| 4,758,483 A | | 7/1988 | Armand et al. | ............. 429/192 |
| 4,851,307 A | | 7/1989 | Armand et al. | ............. 429/192 |
| 4,925,751 A | | 5/1990 | Shackle et al. | ............. 429/191 |
| 5,072,015 A | * | 12/1991 | Fabry et al. | ................. 558/276 |
| 5,232,633 A | * | 8/1993 | Ilardi et al. | ............. 560/186 X |
| 5,356,979 A | | 10/1994 | Tai et al. | ..................... 524/401 |
| 5,460,905 A | | 10/1995 | Skotheim | .................... 429/213 |
| 5,462,566 A | | 10/1995 | Skotheim | ................. 429/213 X |
| 5,514,493 A | | 5/1996 | Waddell et al. | ............. 429/199 |
| 5,587,253 A | | 12/1996 | Gozdz et al. | ................ 429/192 |
| 5,627,292 A | | 5/1997 | Armand et al. | ............. 549/555 |
| 5,652,072 A | | 7/1997 | Lamanna et al. | ........... 429/198 |
| 5,861,224 A | | 1/1999 | Barker et al. | ................ 429/194 |
| 5,883,102 A | | 3/1999 | Hamley et al. | ............. 514/259 |
| 5,922,494 A | | 7/1999 | Barker et al. | ................ 429/342 |
| 6,063,522 A | | 5/2000 | Hamrock et al. | ........... 429/200 |
| 6,114,070 A | | 9/2000 | Yoshida et al. | ............. 429/332 |
| 6,245,465 B1 | * | 6/2001 | Angell et al. | ................ 429/340 |

FOREIGN PATENT DOCUMENTS

| | | |
|---|---|---|
| EP | 0 463 873 A1 | 1/1992 |
| EP | 0359524 B1 | 1/1996 |
| EP | 0858119 A2 | 8/1998 |
| EP | 0887875 A1 | 12/1998 |
| GB | 912 895 A | 12/1962 |
| JP | 11 031526 A | 2/1999 |
| WO | WO 99/19932 | 4/1999 |
| WO | WO 99/30381 | 6/1999 |
| WO | WO 00/08696 | 2/2000 |

OTHER PUBLICATIONS

Y. Ishikawa, et al., "Cyclization of α and β–Alkylthio–Substituted Amines Possessing Positively Charged Carbon at the Nitrogen. A New Synthetic Method for Thiazolidines, Thiomorpholines and Dihydro–1,4–benzothiazines", Chemical and Pharmaceutical Bulletin, vol. 32, No. 2, (Feb. 1984), pp. 438–446, XP002183133.

R. Van Est–Stammer, et al., "Hindered Internal Rotation in Carbamates An NMR study of the conformations of alkyl and aryl N–(alkylsulfonylmethyl)–N–methylcarbamates and aryl N–(arylsulfonylmethyl)–N–methylcarbamates", Recueil Des Travaux Chimiques Des Pays–Bas, vol. 90, No. 12, (Dec. 1971), pp. 1307–1319, XP0022183134.

J. L. Garrido, et al., "One–Step Palladium–Catalyzed Synthesis of Substituted Dihydrofurans from the Carbonate Derivatives of γ–Hydroxy–α,62 –unsaturated Sulfones", Journal of Organic Chemistry, vol. 63, No. 25, (Dec. 11, 1998), pp. 9406–9413, XP002183135.

H. K. Jacobs, et al., "Chiral γ and 67 Hydroxysulfones via Lipase Catalyzed Resolutions Synthesis of (R)(+)4–Hexanolide and (2R,5S)–2–Methyl–5–Hexanolide Using Intramolecular Acylation", Tetrahedron, vol. 48, No. 41, (Oct. 9, 1992), pp. 8891–8898, XP002183136.

V. S. Etlis, et al., "Preparation of Sulfur–Containing Esters of Percarbonic Acid", Journal of General Chemistry of the USSR, vol. 5, No. 4, (1969), pp. 671–674, XP001041441.

M. Reggelin, et al., "Synthesis and Deprotonation of 1–(p–Toluenesulfonyl)–2–Alkenyl Carbamates. Dichotomous Achiral $d^1$ and Chiral $d^3$ Reagents for Carbonyl Addition Directed by Metal Exchange", Tetrahedron Letters, vol. 30, No. 22, (1989), pp. 2915–2918, XP002183138.

E. Toja, et al., "1–Substituted–1,2,5, 6–Tetrahydropyridine–3–Carboxaldehyde–O–Alkyloximes as novel Orally Active and Long–Lasting Muscarinic Cholinergic Agonists", European Journal of Medicinal Chemistry, vol. 27, No. 5, (Aug. 1992), pp. 519–526), XP002183139.

Stanley P. Rowland et al., Reagent effects on distribution of methylsulfonylethyl substituents in the d–glucopyranosyl unit of cotton cellulose, Canadian Journal of Chemistry, vol. 46 pp. 451 thru 457 (1968).

Alex Eberle, Jean–Luc Fauchere, Godefridus Ignatius Tesser, and Robert Schwyzer, Hormone–Receptor Interactions. Synthesis of a–Melanotropin and of Information–Carrying Partial Sequences by Using Alkali–Labile Protecting Groups, Helvetica Chimica Acta—vol. 58, Fasc. 7 (1975)—No. 228, pp. 2106–2129.

Primary Examiner—Richard D. Lovering
(74) Attorney, Agent, or Firm—Lisa M. Thompson; Lucy C. Weiss

(57) ABSTRACT

Novel carbonate compounds and novel carbamate compounds comprise at least one carbonate or carbamate moiety that is directly bonded only to groups selected from the group consisting of alkyl groups, cycloalkyl groups, alkenyl groups, cycloalkenyl groups, alkynyl groups, cycloalkynyl groups, and combinations thereof, the groups optionally containing one or more catenary heteroatoms. At least one of the directly-bonded groups comprises at least one sulfonyl moiety. The compounds are useful as solvents for the electrolyte salts used in electrochemical devices.

22 Claims, No Drawings

OTHER PUBLICATIONS

Johan J.N. Veerman, Floris P.J.T. Rutjes, Jan H. vanMaarseveen and Henk Hiemstra, A Novel Acid Stable/Base Labile Carbamate Linker for N–Acyliminium.

Ion Reactions on Solid Support, Tetrahedron Letters, vol. 40, pp. 6080–6082 (1999).

F.E. Bailey, Jr. and E.M. La Combe Synthesis and Some Properties of Some Sulfonium Polyelectroytes: Polymers and Copolymers Derived from Methylthioethyl Acrylate, J. Macromol. Sci.—Chem., Oct. (1970), A4, pp. 1293–1300.

Kiyokazu Imai, Tomoo Shiomi, Yasuyuki Tezuka, and Matsunori Takada, Synthesis of Sulfone–Modified Poly(vinyl Alcohol) and Its Application for Permselective Membrane of Sulfur Dioxide, Journal of Applied Polymer Science, vol. 35, pp. 1817–1828 (1988).

David Linden, Handbook of Batteries, pp. 36.13–36.16 (1995).

Kirk–Othmer Encyclopedia of Chemical Technology, NY, John Wiley & Sons, (1992) vol. 3, pp. 1107–1115.

B. Scrosati, Modern Batteries, pp. 177–186 (1997), Wiley and Sons, NY.

H.G. Batz, V. Hofmann und H. Ringsdorf, Pharmakologisch aktive Polymere, 4*) Monomere und polymer Alkylsulfiny-l–alkylacrylate und–methacrylate als mogliche Resorptionsvermittler, Die Makromolekulare Chemie, pp. 323–325 (1973).

Saul G. Cohen, Jerome L. Elkind, S. Bano Chishti, Jose–L.P. Giner, Heide Reese, and Jonathan B. Cohen, Effects of Volume and Surface Property in Hydrollysis by Acetylcholinesterase. The Trimethyl Site, J. Med. Chem (1984), vol. 27, pp. 1643–1647.

* cited by examiner

HIGH-BOILING ELECTROLYTE SOLVENT

FIELD OF THE INVENTION

This invention relates to compounds that are useful as solvents for the electrolyte salts used in electrochemical devices. This invention further relates to electrolyte compositions comprising at least one such compound and at least one such salt. In other aspects, this invention also relates to electrochemical devices comprising the electrolyte compositions and to articles comprising the electrochemical devices.

BACKGROUND OF THE INVENTION

The rapid development of electronic devices has increased market demand for electrochemical devices such as fuel cells, capacitors, electrochromic windows, and battery systems. In response to the demand for battery systems in particular, practical rechargeable lithium batteries have been actively researched. These systems are typically based on the use of lithium metal, lithiated carbon, or a lithium alloy as the negative electrode (anode).

Lithium batteries are prepared from one or more lithium electrochemical cells. Such cells have consisted of a non-aqueous lithium ion-conducting electrolyte composition interposed between electrically-separated, spaced-apart positive and negative electrodes. The electrolyte composition is typically a liquid solution of lithium electrolyte salt in nonaqueous aprotic organic electrolyte solvent (often a solvent mixture).

The selection of electrolyte solvents for rechargeable lithium batteries is crucial for optimal battery performance and involves a variety of different factors. However, long-term stability, ionic conductivity, safety, and wetting capability tend to be the most important selection factors in high volume commercial applications.

Long-term stability requires that an electrolyte solvent be intrinsically stable over the battery's range of operating temperatures and voltages and also that it be either unreactive with electrode materials or that it effectively form a passivating film with good ionic conductivity. Ionic conductivity requires an electrolyte solvent that effectively dissolves lithium electrolyte salts and facilitates lithium ion mobility. From the viewpoint of safety, the characteristics of low volatility, low flammability, low combustibility, and low toxicity are all highly desirable. It is also desirable that the battery's electrodes and separator be quickly and thoroughly wetted by the electrolyte solvent, so as to facilitate rapid battery manufacturing and optimize battery performance.

Aprotic liquid organic compounds have been the most commonly used electrolyte solvents for lithium batteries. Often, compounds such as ethers or carbonic acid esters (carbonates) have been utilized, as these compounds typically share the desirable properties of oxidative stability at positive electrodes operating at less than about 4.4 V vs. Li+/Li, low reactivity with lithium-containing negative electrodes, and a thermodynamically favorable interaction with lithium ions (which is manifested in the electrolyte composition as a high degree of dissociation of the anion and the lithium cation of the electrolyte salt).

The most commonly used aprotic organic electrolyte solvents for use in lithium batteries include cyclic esters (for example, ethylene carbonate, propylene carbonate, γ-butyrolactone), linear esters, cyclic ethers (for example, 2-methyltetrahydrofuran, 1,3-dioxolane), linear ethers (for example, 1,2-dimethoxyethane), amides, and sulfoxides. A mixed solvent is sometimes preferred, since the properties of the electrolyte composition (conductance, viscosity, etc.) and its reactivity towards lithium can often be 'tailored' to give optimum performance.

Less traditional solvents such as carboxylic acid esters, sulfoxides, sulfones, and sulfonamides have been used as electrolyte solvents with varying success. Sulfones are typically solids at room temperature. Sulfones such as tetramethylene sulfone (sulfolane) and ethyl methyl sulfone, however, have been used as electrolyte solvents. Dimethylsulfone has also been utilized, but, with a melting point of 107° C., its utility has been limited to batteries that operate at elevated temperatures (that is, at temperatures above which the electrolyte composition can be maintained in the liquid state).

Drawbacks to the use of conventional lithium battery electrolyte solvents are generally related to their low boiling points and high flammabilities or combustibilities. Some solvents, such as the cyclic carbonates ethylene carbonate and propylene carbonate, have boiling points above 200° C. However, many electrolyte solvents have boiling points that are substantially lower and have flash points less than 100° F. Such volatile solvents can ignite during catastrophic failure of a fully or partially charged battery that has undergone, for example, a rapid discharge due to a short circuit. Additionally, volatile solvents present difficulties in the preparation and storage of electrolyte compositions as well as in addition of the composition to the battery during the manufacturing process. Another common problem of some conventional electrolyte solvents is that they often have a surface energy that is too high to spontaneously wet the battery components.

Thus, there remains a need in the art for electrolyte solvents that have reduced volatility, flammability, and combustibility (relative to conventional solvents), yet effectively dissolve electrolyte salts to form stable electrolyte compositions that adequately wet electrochemical device components and that exhibit adequate ionic conductivities over a range of operating temperatures.

SUMMARY OF THE INVENTION

Briefly, in one aspect, this invention provides novel carbonate compounds and novel carbamate compounds that are useful as electrolyte solvents for the electrolyte salts used in electrochemical devices. The compounds comprise at least one carbonate or carbamate moiety that is directly bonded only to groups selected from the group consisting of alkyl groups, cycloalkyl groups, alkenyl groups, cycloalkenyl groups, alkynyl groups, cycloalkynyl groups, and combinations thereof (for example, cycloalkyl-substituted alkyl groups), the groups optionally containing one or more catenary heteroatoms. (As used herein, the term "catenary heteroatoms" means heteroatoms (for example, nitrogen, oxygen, or sulfur) that replace one or more carbon atoms of a group in a manner such that the heteroatom is bonded to at least two carbon atoms of the group.) At least one of the directly-bonded groups comprises at least one sulfonyl moiety.

Preferably, the compounds are sulfonyl-containing dialkyl carbonate compounds. More preferably, the compounds are sulfonyl-containing dialkyl carbonate compounds comprising lower alkyl groups that each contain no more than about six (most preferably, no more than about four) carbon atoms.

It has been discovered that the above-described novel compounds have surprisingly high boiling points and low volatilities and thus, in general, are less flammable and less combustible than conventional electrolyte solvents. Yet the compounds quite effectively dissolve electrolyte salts to provide electrolyte compositions that adequately wet electrochemical device components (such as separators) and that exhibit adequate ionic conductivities for use in electrochemical devices over a range of operating temperatures (for example, from about 20° C. to about 80° C. or even higher, depending upon the power requirements for a particular application). The compounds (and electrolyte compositions comprising the compounds) also present fewer difficulties in storage and handling than do conventional materials, due to their lower volatility, flammability, and combustibility.

The compounds are particularly well-suited for use in high-temperature batteries (batteries that are designed to function at temperatures above, for example, about 60° C.). In such batteries, electrolyte compositions comprising the compounds exhibit adequate conductivities, while being less likely to ignite during catastrophic battery failure than conventional electrolyte compositions.

Thus, the novel compounds of the invention meet the need in the art for electrolyte solvents that have reduced volatility, flammability, and combustibility (relative to conventional solvents), yet effectively dissolve electrolyte salts to form stable electrolyte compositions that adequately wet electrochemical device components and that exhibit adequate ionic conductivities over a range of operating temperatures.

In other aspects, this invention also provides electrolyte compositions comprising (a) at least one compound of the invention, and (b) at least one electrolyte salt; electrochemical devices comprising the electrolyte compositions; and articles comprising the electrochemical devices.

DETAILED DESCRIPTION OF THE INVENTION

Electrolyte Solvents

The novel compounds of the invention comprise at least one (preferably, only one) carbonate or carbamate moiety (preferably, carbonate) that is directly bonded only to alkyl, cycloalkyl, alkenyl, alkynyl, cycloalkynyl, or cycloalkenyl groups, or to combinations thereof (for example, cycloalkyl-containing alkyl groups, cycloalkyl-containing alkenyl groups, cycloalkenyl-containing alkyl groups, and cycloalkenyl-containing alkenyl groups, where the cyclic moiety can be either monovalent or divalent depending upon its location within the alkyl or alkenyl group). (Thus, the carbonate or carbamate moiety is directly bonded only to groups other than aryl groups or aryl-containing groups.) Preferably, the carbonate or carbamate moiety is bonded only to alkyl groups. At least one of the directly-bonded groups (preferably, only one) comprises at least one sulfonyl moiety (preferably, only one such moiety). Although the directly-bonded groups can optionally contain one or more catenary heteroatoms (for example, nitrogen, oxygen, or sulfur atoms), preferred compounds contain no catenary heteroatoms other than the sulfur atom of the sulfonyl moiety. Preferably, the directly-bonded groups each contain no more than about six carbon atoms (more preferably, no more than about four), so that the ratio of the number of oxygen atoms to the number of carbon atoms in the compound is in the range of about 0.4 to about 1 (more preferably, from about 0.66 to about 1; most preferably, from about 0.83 to about 1).

A preferred class of the novel compounds of the invention is that which can be represented by the following general formula (I):

$$H(CH_2)_mSO_2(CH_2)_nQ(R)_p \qquad (I)$$

wherein Q is a carbonate moiety, —O—C(O)—O—, or a carbamate moiety, —O—C(O)—N— (preferably, a carbonate moiety); each R is independently a group selected from the group consisting of alkyl groups, cycloalkyl groups, alkenyl groups, cycloalkenyl groups, alkynyl groups, cycloalkynyl groups, and combinations thereof (preferably, alkyl groups), the groups optionally containing one or more catenary heteroatoms; m is an integer of one to about four; n is an integer of one to about four; and p is an integer of 1 when Q is a carbonate moiety and is an integer of 2 when Q is a carbamate moiety. Preferably, R contains no catenary heteroatoms, R has no more than about six carbon atoms (more preferably, no more than about four carbon atoms), and the sum of m and n is less than or equal to about six (more preferably, less than or equal to about four).

Representative examples of the compound of the invention include:

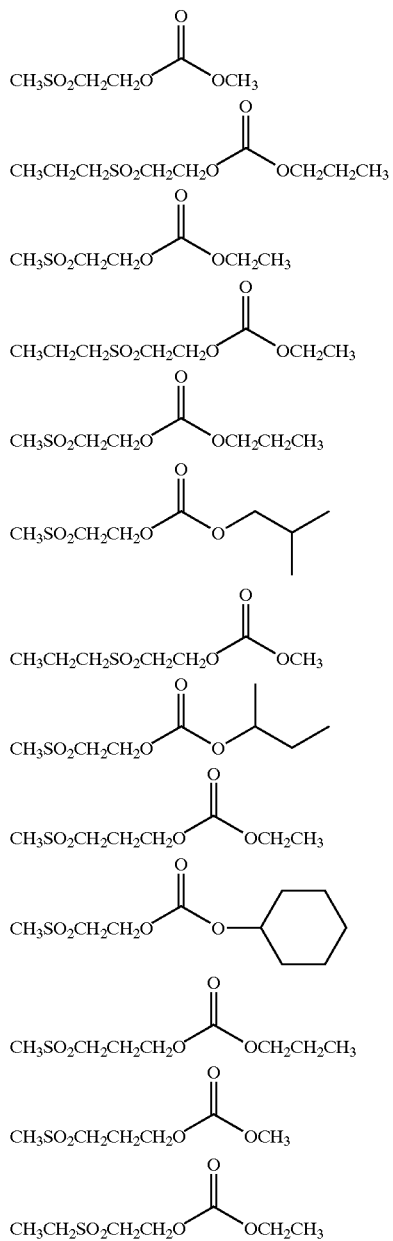

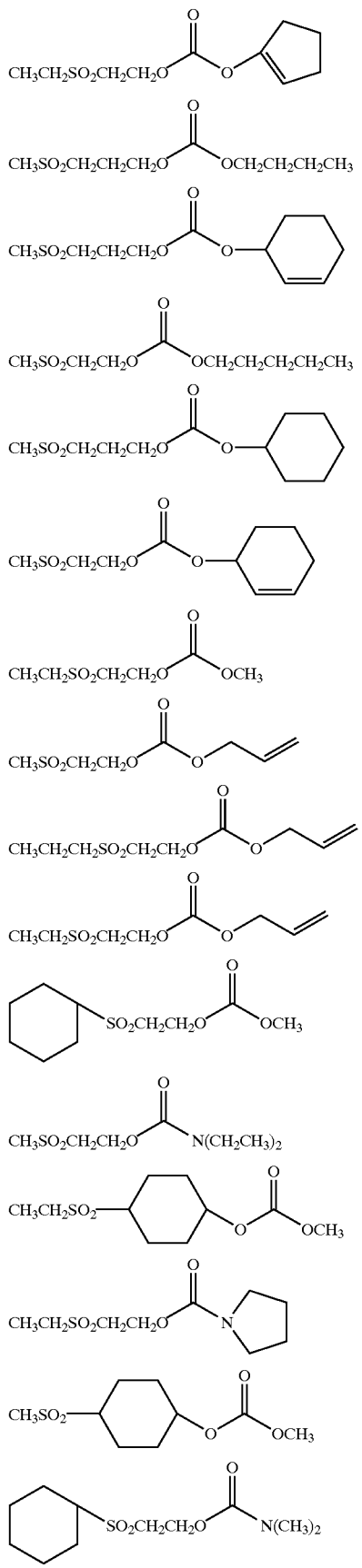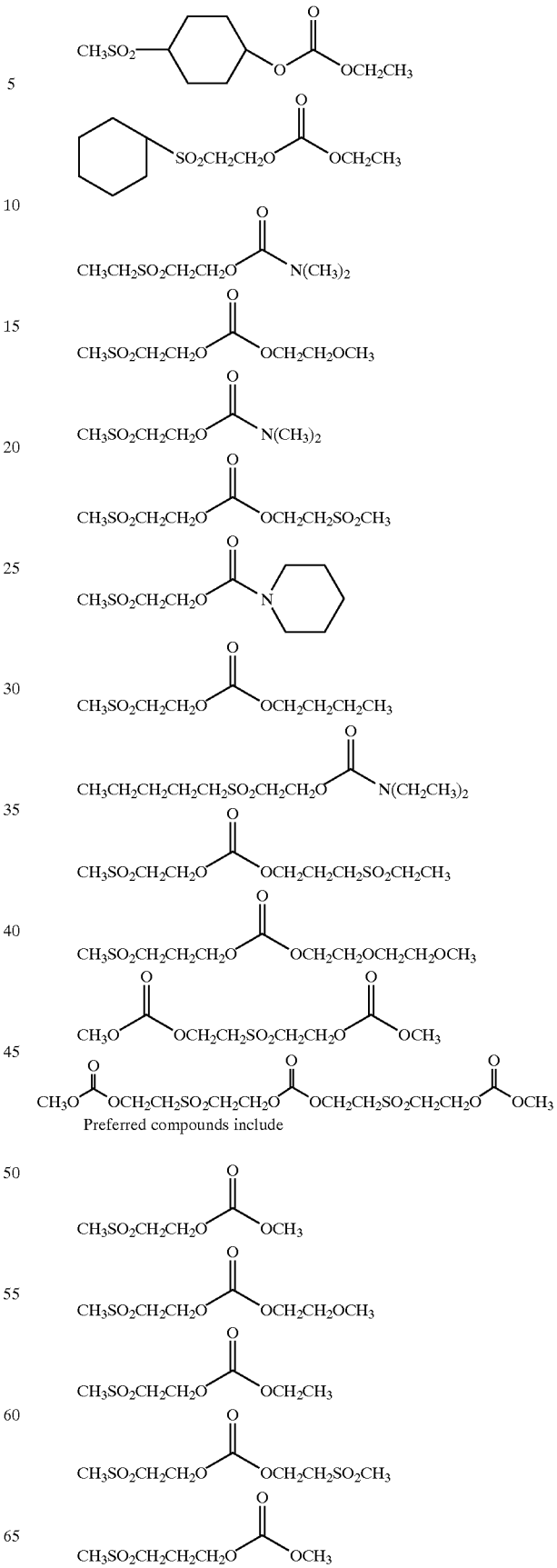

-continued

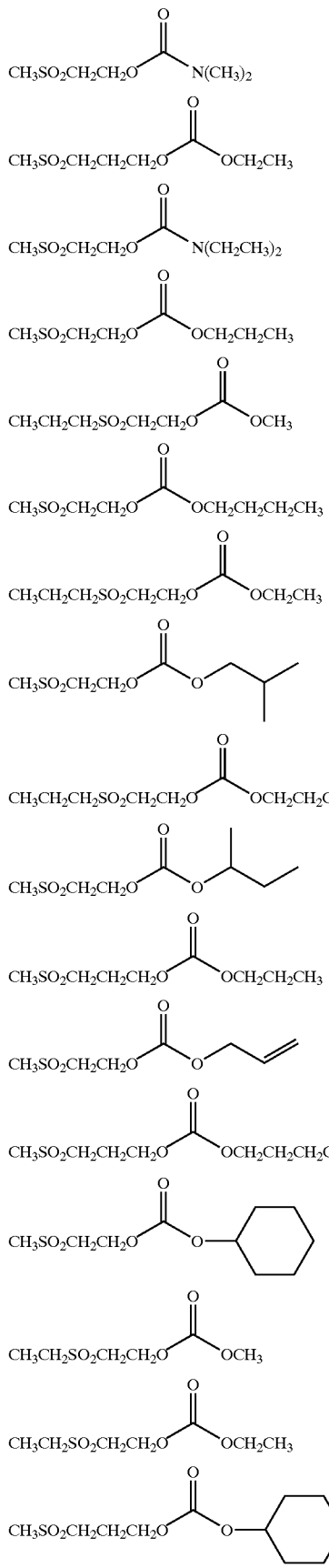

-continued

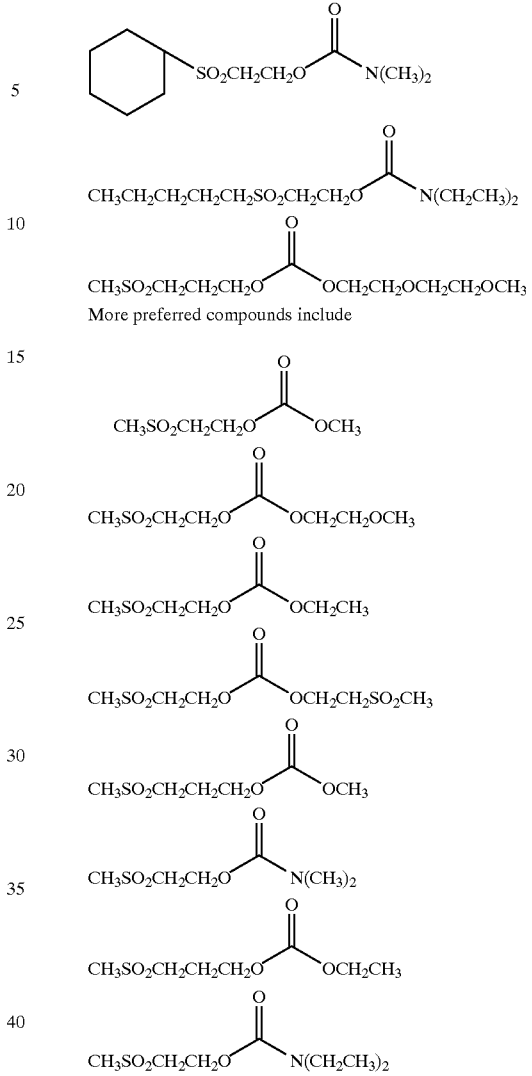

More preferred compounds include

The compounds of the invention can be prepared by combining (preferably, in the presence of a base or hydrogen ion acceptor, and, optionally, in an organic solvent) (a) an alcohol comprising at least one sulfonyl moiety and (b) an alcohol-reactive compound (for example, a carbonic acid halide or a carbamic acid halide) that is capable of reacting with the alcohol to form a carbonate (a carbonic acid ester) or a carbamate (a carbamic acid ester) via a condensation reaction (with the elimination of, for example, a mineral acid). Reactions of this type are well-known in organic chemistry and have been described, for example, by Jerry March in *Advanced Organic Chemistry*, 4th Edition, p. 392, John Wiley & Sons, New York (1992).

Preferably, a base or hydrogen ion acceptor (more preferably, an organic base such as an amine) is present to neutralize any mineral acid that is generated during the condensation reaction. Examples of useful organic bases include heterocyclic aromatic amines (for example, pyridine) and alkylamines (for example, diisopropylamine and triethylamine). Those skilled in the art will recognize the types and limitations of organic bases that are useful for such condensation reactions.

Alcohols that can be used to prepare the compounds of the invention include primary, secondary, and tertiary alcohols (preferably, primary or secondary; more preferably, primary)

that comprise at least one sulfonyl moiety, but that do not comprise interfering functional groups (for example, groups such as primary amine, thiol, or carboxylic acid groups, which can interfere with the reaction of the alcohol by reacting with the alcohol-reactive compound; or groups such as isocyanate, carboxylic acid, acyl halide, and ester groups, which can react with the hydroxyl group of the alcohol itself). Representative examples of suitable alcohols include:

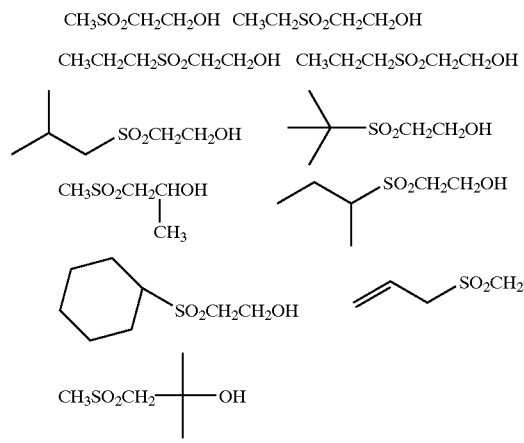

and the like, and mixtures thereof.

Compounds that are suitable for use as the alcohol-reactive compound comprise a hydroxyl-reactive functional group (for example, an acid halide-group) that is capable of reacting with the hydroxyl group of an alcohol in a condensation reaction to form a carbonate or a carbamate, with the elimination of a small molecule (for example, a mineral acid such as hydrochloric acid). The compounds preferably have one such hydroxyl-reactive functional group, although it is understood that the products of reactions of compounds with more than one such hydroxyl-reactive functional group are within the scope of this invention. The alcohol-reactive compounds do not comprise other functional groups (such as, for example, alcohol, amine, thiol, or carboxylic acid groups) that are capable of reacting with the hydroxyl-reactive functional group.

Suitable alcohol-reactive compounds include derivatives of formic acid (for example, alkyl haloformates, such as ethyl chloroformate and methyl chloroformate; alkenyl haloformates; cycloalkyl haloformates; and cycloalkenyl haloformates) and nitrogen-containing compounds that are isoelectronic with such formic acid derivatives (for example, alkyl halocarbamates, such as dimethyl chlorocarbamate; alkenyl halocarbamates; cycloalkyl halocarbamates; and cycloalkenyl halocarbamates). Representative examples of suitable alcohol-reactive compounds include:

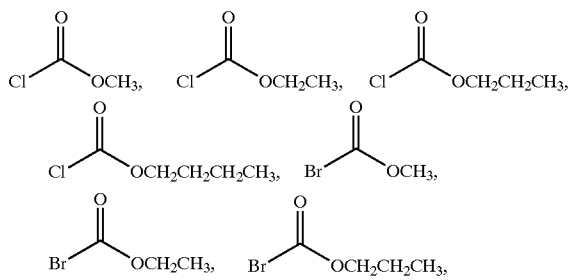

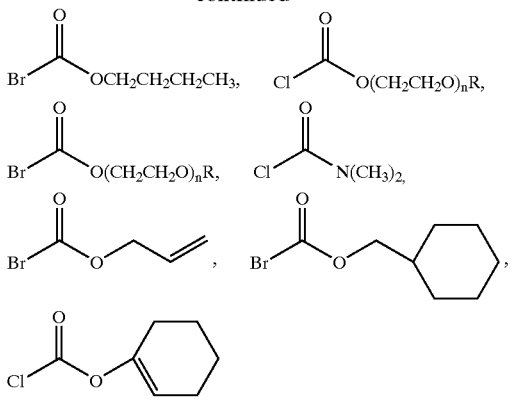

If desired, alcohol-reactive compounds that contain one or more sulfonyl moieties can be utilized. For example, a sulfonyl-containing alcohol can be allowed to react with phosgene to provide a sulfonyl-containing chloroformate, followed by the reaction of the sulfonyl-containing chloroformate with an alcohol. This two-step process can be carried out by using the same alcohol in both steps, or by using two different alcohols. This process is a preferred process for preparing symmetrical carbonate compounds comprising at least two sulfonyl moieties, as shown for example below:

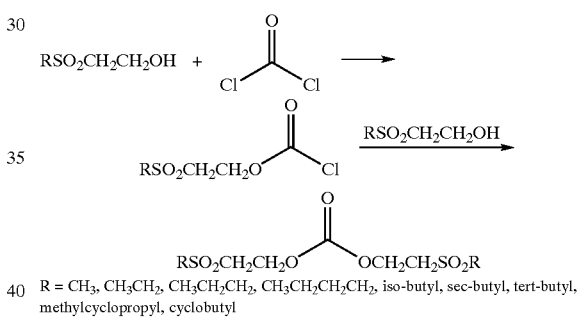

R = CH$_3$, CH$_3$CH$_2$, CH$_3$CH$_2$CH$_2$, CH$_3$CH$_2$CH$_2$CH$_2$, iso-butyl, sec-butyl, tert-butyl, methylcyclopropyl, cyclobutyl The two reactants (the alcohol and the alcohol-reactive compound) can be added to a reaction vessel in any order. The condensation reaction can be carried out at any of a range of temperatures, depending upon whether a sealed or unsealed reaction vessel is utilized. However, it is generally preferable to carry out the reaction at temperatures below the boiling point of the lower boiling reactant (for example, at temperatures between about −10° C. and about 50° C.; more preferably, between about 0° C. and about 25° C.) in an open vessel.

If desired, the reaction can be carried out in a relatively polar organic solvent (for example, a solvent such as tetrahydrofuran, glyme, chloroform, 1,2-dichloroethane, diethyl ether, tert-butyl methyl ether, and the like, and mixtures thereof). Preferably, no organic solvent is used, but the reaction is carried out in the presence of an excess of base. The desired product can be isolated by adding the resulting reaction mixture to water (or to aqueous mineral acid, if base has been utilized) and then extracting the product with a slightly polar solvent (for example, dichloromethane).

A preferred process for preparing the compounds of the invention comprises the steps of 1) combining an alcohol with an about 5% to about 100% molar excess of organic amine in a reaction vessel at about 0° C.; 2) adding an alcohol-reactive compound to the vessel at a rate sufficient to maintain the temperature of the resulting reaction mixture at about 0° C.; 3) allowing the reaction mixture to warm to room temperature; 4) adding the reaction mixture to aqueous mineral acid; 5) extracting the desired product with a solvent in which the product is soluble; 6) drying the resulting solution of the product with a conventional solid drying agent (for example, anhydrous sodium sulfate); and 7) removing the solvent by evaporation to isolate the product. The isolated product can then be purified, if desired, by conventional methods such as chromatography, distillation, crystallization, etc., all of which are well-known to those skilled in the art.

An alternative process for preparing the compounds of the invention involves transesterification, which is described, for example, by Jerry March in *Advanced Organic Chemistry*, 4$^{th}$ Edition, pp. 397–398, John Wiley & Sons, New York (1992). This process involves combining (a) an alcohol comprising at least one sulfonyl moiety, as described above (except less preferably in this case a tertiary alcohol) and (b) a carbonate compound (preferably, a symmetrical carbonate compound), with heating and in the presence of a catalyst such as a strong acid, a strong base, or a high-valency early transition metal complex (for example, Ti(IV) propoxide). This process can also be used to prepare symmetrical carbonate compounds comprising more than one sulfonyl moiety, as shown for example below:

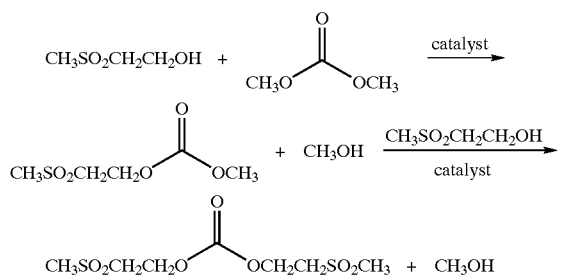

Electrolyte Compositions

The compounds of the invention can be utilized to prepare electrolyte compositions comprising (a) at least one compound of the invention; and (b) at least one electrolyte salt. Electrolyte salts that are suitable for use in preparing the electrolyte compositions of the invention include those salts that comprise at least one cation and at least one weakly coordinating anion, that are at least partially soluble in a selected compound of the invention (or in a blend thereof with one or more other compounds of the invention or one or more conventional electrolyte solvents), and that at least partially dissociate to form a conductive electrolyte composition. Preferably, the salts are stable over a range of operating voltages, are non-corrosive, and are thermally and hydrolytically stable.

Suitable cations include alkali metal, alkaline earth metal, Group IIB metal, Group IIIB metal, transition metal, rare earth metal, and ammonium (for example, tetraalkylammonium or trialkylammonium) cations, as well as a proton. Preferred cations for battery use include alkali metal and alkaline earth metal cations.

Suitable weakly coordinating anions include $NO_3^-$; $Br^-$; $I^-$; $BF_4^-$; $PF_6^-$; $AsF_6^-$; $ClO_4^-$; $SbF_6^-$; $HSO_4^-$; $H_2PO_4^-$; organic anions such as alkane, aryl, and alkaryl sulfonates; fluorinated and unfluorinated tetraarylborates; carboranes and halogen-, alkyl-, or haloalkyl-substituted carborane anions including metallocarborane anions; teflates (for example, $^-OTeF_5$, $^-B(OTeF_5)_4$, and $^-Pd(OTeF_5)_4$); and fluoroorganic anions such as perfluoroalkanesulfonates, cyanoperfluoroalkanesulfonylamides, bis(cyano) perfluoroalkanesulfonylmethides, bis(perfluoroalkanesulfonyl)imides, bis(perfluoroalkanesulfonyl)methides, and tris(perfluoroalkanesulfonyl)methides; and the like. Preferred anions for battery use include fluoroinorganic anions (for example, $BF_4^-$, $PF_6^-$, and $AsF_6^-$) and fluoroorganic anions (for example, perfluoroalkanesulfonates, bis(perfluoroalkanesulfonyl)imides, and tris(perfluoroalkanesulfonyl)methides).

The fluoroorganic anions can be either fully fluorinated, that is perfluorinated, or partially fluorinated (within the organic portion thereof). Preferably, the fluoroorganic anion is at least about 80 percent fluorinated (that is, at least about 80 percent of the carbon-bonded substituents of the anion are fluorine atoms). More preferably, the anion is perfluorinated (that is, fully fluorinated, where all of the carbon-bonded substituents are fluorine atoms). The anions, including the preferred perfluorinated anions, can contain one or more catenary heteroatoms such as, for example, nitrogen, oxygen, or sulfur.

Preferred fluoroorganic anions include perfluoroalkanesulfonates, bis(perfluoroalkanesulfonyl)imides, and tris(perfluoroalkanesulfonyl)methides. The perfluoroalkanesulfonates and bis(perfluoroalkanesulfonyl)imides are more preferred anions, with the perfluoroalkanesulfonates being most preferred.

Preferred salts for battery use are lithium salts. More preferred are lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide or a mixture thereof.

The electrolyte compositions of the invention can be prepared by combining at least one compound of the invention and at least one electrolyte salt such that the salt is at least partially dissolved in the compound of the invention at the desired operating temperature. One or more conventional electrolyte solvents (for example, propylene carbonate or dimethoxyethane) or other conventional additives (for example, a surfactant) can also be present, if desired. The electrolyte salt is preferably employed at a concentration such that the conductivity of the electrolyte composition is at or near its maximum value (typically, for example, at a $Li^+$ molar concentration of around 0.5–2.0 M, preferably about 1.0 M, for electrolytes for lithium batteries), although a wide range of other concentrations will also serve.

Electrochemical Devices

The electrolyte compositions of the invention can be used as electrolytes in electrochemical devices including, for example, such devices as fuel cells, batteries, capacitors, and electrochromic windows. Such devices typically comprise at least one first electrode, at least one second electrode, at least one separator, and an electrolyte composition of the invention.

The electrodes of, for example, a lithium battery generally consist of a metallic foil or particles of active material blended with a conductive diluent such as carbon black or graphite bound into a polymeric material binder. Typical binders include polytetrafluoroethylene, polyvinylidene fluoride, ethylene-propylene-diene (EPDM) terpolymer, and emulsified styrene-butadiene rubber (SBR), and the binder can be cross-linked. The binder can also be, for example, a solid carbon matrix formed from the thermal decomposition of an organic compound. The metallic foil or composite electrode material is generally applied to an expanded metal screen or metal foil (preferably aluminum, copper, nickel, or stainless steel) current collector using any of a variety of processes such as coating, casting, pressing or extrusion.

Some examples of suitable first electrodes are lithium metal, aluminum, lithium metal alloys, sodium metal, platinum and palladium and alloys thereof, carbon-based materials such as graphite, coke, carbon, pitch, transition metal oxides (for example, $LiTi_5O_{12}$ and $LiWO_2$), and lithiated tin oxide. In the case of lithium ion batteries, the lithium can be intercalated into a host material such as carbon (that is, to give lithiated carbon) or carbon alloyed with other elements (such as silicon, boron or nitrogen), a conductive polymer, or an inorganic host that is intercalatable (such as $Li_xTi_5O_{12}$). The material comprising the first electrode can be carried on foil (for example, nickel and copper) backing or pressed into expanded metal screen and alloyed with various other metals.

Active second electrode materials generally provide device voltages of at least about 3.0 volts at a full state of charge relative to $Li/Li^+$. Suitable second electrode materials include graphite; carbon; aluminum; $MnO_2$; platinum, palladium, and alloys thereof; a composite oxide comprising Li and a transition metal such as $LiCoO_2$, $LiNiO_2$, $LiV_3O_8$, $LiMn_2O_4$, etc.; $V_2O_5$; $V_6O_{13}$; $Ba_2SmNiO_5$; $SmMnO_3$; $Sm_3Fe_5O_{12}$; $EuFeO_3$; $EuFe_5O_{12}$; $EuMnO_3$; $LaNiO_3$; $La_2CoO_4$ and $LaMnO_3$ (including the charged and discharged forms of these materials); oxides of ruthenium or tungsten; indium tin oxide; and conducting polymers such as polypyrrole, polysulfides and polyvinylferrocene. In primary batteries, the second electrode can be fluorinated carbon (for example, $(CF)_n$), $SO_2Cl_2$, $Ag_2V_4O_{11}$, $Ag_2CrO_4$, sulfur, polysulfide, or an $O_2$ or $SO_2$ electrode.

Lithium batteries generally contain a separator to prevent short-circuiting between the first and second electrodes. The separator often consists of a single-ply or multi-ply sheet of microporous polymer (typically polyolefin, for example, polyethylene, polypropylene, or combinations thereof) having a predetermined length and width and having a thickness of less than about 1.0 mil (0.025 mm). For example, see U.S. Pat. No. 3,351,495 (Larsen et al.), U.S. Pat. No. 4,539,256 (Shipman et al.), U.S. Pat. No. 4,731,304 (Lundquist et al.) and U.S. Pat. No. 5,565,281 (Yu et al.). The pore size in these microporous membranes, typically about 5 microns in diameter, is sufficiently large to allow transport of ions but is sufficiently small to prevent electrode contact, either directly or from particle penetration or dendrites which can form on the electrodes.

The electrochemical devices of the invention can be used in various electronic articles such as computers, power tools, automobiles, telecommunication devices, and the like.

Objects and advantages of this invention are further illustrated by the following examples, but the particular materials and amounts thereof recited in these examples, as well as other conditions and details, should not be construed to unduly limit this invention. In the following examples, the structures of prepared compounds were determined using nuclear magnetic resonance spectroscopy, infrared spectroscopy, and mass spectrometry. Column chromatography was conducted on silica gel, using a mixture of one part by volume acetonitrile and 2 parts by volume chloroform.

EXAMPLES

Example 1
Preparation of 2-(Methylsulfonyl)ethyl Methyl Carbonate

A 100 ml 3-neck round bottom flask, fitted with a magnetic stir bar, rubber septum and hose adapter, was flushed with dry nitrogen and was charged via syringe with 9.82 g (0.0791 mol) 2-(methylsulfonyl) ethanol (Aldrich Chemical Co., Milwaukee, Wis.) and 25 ml anhydrous pyridine. The resulting mixture was cooled in an ice-water bath for 15 minutes. Methyl chloroformate (8.30 g; 0.088 mol) was added dropwise to the mixture via syringe over 20 minutes. The ice-water bath was then removed, and the mixture was allowed to stir at room temperature. After 4 hours, the resulting light yellow mixture was poured into 120 ml of ice cold 10% aqueous HCl in a separatory funnel, and the resulting solution was extracted four times with 40 ml aliquots of $CH_2Cl_2$. The resulting organic extracts were combined and dried over $Na_2SO_4$. Solvent removal under reduced pressure on a rotary evaporator left a clear light yellow liquid, which was purified by column chromatography to yield 11.7 g (81% yield) of the 2-(methylsulfonyl) ethyl methyl carbonate as a clear very pale yellow oil, which solidified at room temperature. A portion of the oil was recrystallized from diethyl ether to give white needles, m.p. 47–48.5° C.

Example 2
Preparation of 2-(Methylsulfonyl)ethyl Ethyl Carbonate

A 100 ml 3-neck round bottom flask, fitted with a magnetic stir bar, rubber septum and hose adapter, was flushed with dry nitrogen and was charged via syringe with 9.61 g (0.0774 mol) 2-(methylsulfonyl) ethanol (Aldrich Chemical Co., Milwaukee, Wis.) and 25 ml anhydrous pyridine. The resulting mixture was cooled in an ice-water bath for 15 minutes. Ethyl chloroformate (9.48 g; 0.087 mol) was added dropwise to the mixture via syringe over 20 minutes. The ice-water bath was then removed, and the mixture was allowed to stir at room temperature. After 5 hours, the resulting light yellow mixture was poured into 120 ml of ice cold 10% aqueous HCl in a separatory funnel, and the resulting solution was extracted four times with 50 ml aliquots of $CH_2Cl_2$. The resulting organic extracts were combined and washed with 60 ml saturated aqueous NaCl and were then dried over $Na_2SO_4$. Solvent removal under reduced pressure on a rotary evaporator left a clear light yellow liquid, which was purified by column chromatography to yield 14.62 g (96% yield) of the 2-(methylsulfonyl) ethyl ethyl carbonate as a clear colorless oil. Vacuum distillation at $8.5 \times 10^{-3}$ mm Hg of a portion of the resulting purified liquid gave a clear oil, b.p. 121–124° C.

Example 3
Preparation of 3-(Methylsulfonyl)propyl Methyl Carbonate

A 250 ml round bottom flask, open to the atmosphere and fitted with a magnetic stir bar and heating mantle, was charged with 24.74 g (0.233 mol) 3-methylthio-1-propanol (Aldrich Chemical Co., Milwaukee, Wis.), 24 ml $H_2O$ and 0.0300 g disodium tungstate dihydrate. Over the course of 40 minutes, 56.96 g 30% aqueous $H_2O_2$ (hydrogen peroxide) was added dropwise via pipette to the resulting mixture. The reaction was exothermic, and the resulting mixture was allowed to cool occasionally during the addition of the $H_2O_2$. The mixture was then heated to 60–70° C. for 3.5 hours, after which time the test for peroxide (Merck peroxide test strips) was negative. Additional $H_2O_2$ solution (2.0 g) was added to the mixture, and the mixture was stirred for one additional hour. The small amount of excess $H_2O_2$ in the mixture was destroyed by the addition of 10% aqueous sodium bisulfite solution. Removal of water under reduced pressure on a rotary evaporator provided a slightly hazy colorless liquid, which was purified by vacuum distillation at $10^{-3}$ mm Hg to yield 19.12 g (59.4% yield) of 3-(methylsulfonyl)-1-propanol as a clear colorless liquid, b.p. 136–139° C.

A 100 ml 3-neck round bottom flask, fitted with a magnetic stir bar, rubber septum and hose adapter, was flushed with dry nitrogen and was charged via syringe with 17.53 g (0.127 mol) 3-(methylsulfonyl)-1-propanol and 19 ml anhydrous pyridine. The resulting mixture was cooled in an ice-water bath. Methyl chloroformate (13.3 g; 0.141 mol) was added dropwise to the mixture via syringe over 45 minutes. The ice-water bath was then removed, and the mixture was allowed to stir at room temperature. After 3.5 hours, the resulting white opaque mixture was poured into 120 ml of ice cold 10% aqueous HCl in a separatory funnel, and the resulting solution was extracted four times with 50 ml aliquots of $CH_2Cl_2$. The resulting organic extracts were combined and dried over $Na_2SO_4$. Solvent removal under reduced pressure on a rotary evaporator left a clear pale yellow liquid, which solidified as it cooled. The resulting solid was purified by recrystallization from t-butyl methyl ether to give 17.6 g of white needles, m.p. 55–56.5° C., and a filtrate that was then concentrated to provide a second batch of crystals (1.9 g), m.p. =55–57° C., to yield a total of 19.5 g (78% yield) of 3-(methylsulfonyl) propyl methyl carbonate.

Example 4
Preparation of an Electrolyte Composition Comprising Ethyl 2-(Methylsulfonyl)ethyl Carbonate An electrolyte composition was prepared by dissolving 0.96 g (6.15 mmol) of lithium trifluoromethanesulfonate (Fluorad™ FC-122, 3M Company) in 6.15 g of ethyl 2-(methylsulfonyl) ethyl carbonate prepared essentially according to the procedure given in Example 2. The resulting electrolyte solution was transferred to a 15 mm diameter test tube. A YSI™ conductivity cell with a cell constant of 1.0 (manufactured by Yellow Springs Instrument Co., Inc., Yellow Springs, Ohio; available from VWR Scientific Products) was inserted into the test tube. The impedance of the electrolyte solution was measured at 26° C. using a Solartron™ Model 1260 Impedance Analyzer with a Solartron™ Model 1287 Electrochemical Interface (available from Solartron Instruments, Houston, Tex.). The impedance of the electrolyte solution was found to be 38,500 ohms, which corresponds to a conductivity of $2.6 \times 10^{-5}$ S/cm. The test tube was then placed in a solid aluminum block heater, which was thermostatically controlled with an Omega™ Model CN 76000 temperature controller set at 50° C. The impedance of the solution was again measured and was determined to be 11,600 ohms, which corresponds to a conductivity of $8.6 \times 10^{-5}$ S/cm.

Example 5
Preparation of an Electrolyte Composition Comprising Ethyl 2-(Methylsulfonyl)ethyl Carbonate An electrolyte composition was prepared by dissolving 1.175 g (4.09 mmol) of lithium bis (trifluoromethanesulfonyl) imide (Fluorad™ HQ-115, 3M Company) in 4.09 g of ethyl 2-(methylsulfonyl) ethyl carbonate prepared essentially according to the procedure given in Example 2. The resulting electrolyte solution was transferred to a 15 mm diameter test tube. A YSI™ conductivity cell with a cell constant of 1.0 (manufactured by Yellow Springs Instrument Co., Inc., Yellow Springs, Ohio; available from VWR Scientific Products) was inserted into the test tube. The impedance of the electrolyte solution was measured at 26° C. using a Solartron™ Model 1260 Impedance Analyzer with a Solartron™ Model 1287 Electrochemical Interface (available from Solartron Instruments, Houston, Tex.). The impedance of the electrolyte solution was found to be 9,600 ohms, which corresponds to a conductivity of $1.0 \times 10^{-4}$ S/cm Example 6
Preparation of Electrochemical Cells Comprising the Electrolyte Composition of Example 4

An electrode was made by combining $MnO_2$ (Aldrich Chemical Co., Milwaukee, Wis., <10 micron, heated in a furnace at 400° C. for 18 hours) with Vulcan™ VXC-72 conductive carbon (Cabot Corporation) and a solution of poly (vinylidene fluoride) (PVDF) in N-methylpyrrolidone. The weight ratio of $MnO_2$ to Vulcan™ VXC-72 conductive carbon to PVDF was 90:5:5. The resulting suspension was coated onto 1 micron-thick stainless steel foil at a wet thickness of 0.254 mm (0.010"). The resulting coated foil was dried in an oven at 80° C. for 20 minutes and was further dried in a vacuum oven at 120° C. for 12 hours. Electrochemical cells (2325 coin cells) were assembled with the coated foil as one electrode, lithium metal as the counter electrode, and the electrolyte composition of Example 4 as the electrolyte. One layer of Cotran™ 9711 microporous poly(ethylene) (3M Company) was used as separator material. The electrodes and the separator were observed to be thoroughly wetted by the electrolyte composition prior to closing the cells. The resulting electrochemical cells had an open circuit voltage between 3.1 V and 3.5 V. The electrochemical cells were discharged to 0.5 V on a Maccor™ Series 2000 Battery Tester (Maccor Inc., Tulsa, Okla.).

Various modifications and alterations of this invention will become apparent to those skilled in the art without departing from the scope and spirit of this invention.

What is claimed is:

1. A compound comprising at least one carbonate or carbamate moiety that is directly bonded only to directly-bonded groups selected from the group consisting of alkyl groups, cycloalkyl groups, alkenyl groups, cycloalkenyl groups, alkyl groups, cycloalkynyl groups, and combinations thereof, said groups optionally containing one or more catenary heteroatoms, at least one said directly-bonded group comprising at least one sulfonyl moiety, and said carbamate moiety being bonded to said directly-bonded group comprising at least one sulfonyl moiety only through its single-bonded oxygen atom.

2. The compound of claim 1 wherein said carbonate or carbamate moiety is a carbonate moiety.

3. The compound of claim 1 comprising only one said carbonate or carbamate moiety.

4. The compound of claim 1 wherein said directly-bonded groups are alkyl groups.

5. The compound of claim 1 wherein said directly-bonded groups do not contain catenary heteroatoms other than the sulfur atom of said at least one sulfonyl moiety.

6. The compound of claim 1 wherein only one said directly-bonded group comprises at least one said sulfonyl moiety.

7. The compound of claim 1 wherein said at least one directly-bonded group comprises only one said sulfonyl moiety.

8. The compound of claim 1 having an oxygen content and a carbon content such that the ratio of its number of oxygen atoms to its number of carbon atoms is in the range of about 0.4 to about 1.

9. The compound of claim 1 wherein said directly-bonded groups each contain no more than about six carbon atoms.

10. The compound of claim 9 wherein said groups each contain no more than about four carbon atoms.

11. A compound of claim 1 that is represented by the following general formula I:

wherein Q is a carbonate moiety, —O—C(O)—O—, or a carbamate moiety,

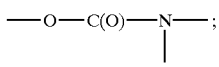

each R is independently a group selected from the group consisting of alkyl groups, cycloalkyl groups, alkenyl groups, cycloalkenyl groups, alkynyl groups, cycloalkynyl groups, and combinations thereof, said groups optionally containing one or more catenary heteroatoms; m is an integer of one to about four; n is an integer of one to about four; and p is an integer of 1 when Q is a carbonate moiety and is an integer of 2 when Q is a carbamate moiety.

12. The compound of claim 11 wherein said Q is a carbonate moiety.

13. The compound of claim 11 wherein each said R group is an alkyl group that optionally contains one or more catenary heteroatoms.

14. The compound of claim 11 wherein each said R does not contain catenary heteroatoms.

15. The compound of claim 11 wherein the sum of m and n is less than or equal to about six.

16. A composition comprising (a) at least one compound of claim 1; and (b) at least one electrolyte salt.

17. An electrochemical device comprising the composition of claim 16.

18. An article comprising the electrochemical device of claim 17.

19. A compound that is represented by the following general formula I:

wherein Q is a carbonate moiety, —O—C(O)—O—; R is an alkyl group that contains no more than about six carbon atoms and that optionally contains one or more catenary heteroatoms; m is an integer of one to about four; n is an integer of one to about four; p is an integer of 1; and the sum of m and n is less than or equal to about six.

20. A composition comprising (a) at least one compound of claim 19; and (b) at least one electrolyte salt.

21. An electrochemical device comprising the composition of claim 20.

22. An article comprising the electrochemical device of claim 21.

* * * * *